United States Patent [19]

Inbar et al.

[11] Patent Number: 4,588,897
[45] Date of Patent: May 13, 1986

[54] GAMMA CAMERA CORRECTION SYSTEM AND METHOD FOR USING THE SAME

[75] Inventors: Dan Inbar; Giora Gafni, both of Haifa; Ernest Grimberg, Kiryat Bialick; Jacob Koren, Haifa, all of Israel

[73] Assignee: Elscint, Ltd., Haifa, Israel

[21] Appl. No.: 483,741

[22] Filed: Apr. 11, 1983

Related U.S. Application Data

[63] Continuation of Ser. No. 161,050, Jun. 19, 1980, Pat. No. 4,424,446.

[51] Int. Cl.$^4$ ............................................. G01T 1/209
[52] U.S. Cl. ................................. 250/363 S; 250/369
[58] Field of Search ............ 250/361 R, 363 R, 363 S, 250/366, 369

[56] References Cited

U.S. PATENT DOCUMENTS

| | | | |
|---|---|---|---|
| 3,745,345 | 7/1973 | Muehllehner | 250/363 S |
| 3,978,336 | 8/1976 | Roux | 250/366 |
| 4,095,108 | 6/1978 | Inbar et al. | 250/363 S |
| 4,151,416 | 4/1979 | Richey et al. | 250/363 S |
| 4,212,061 | 7/1980 | Knoll et al. | 250/363 S |
| 4,223,221 | 9/1980 | Gambini et al. | 250/369 |
| 4,223,388 | 9/1980 | Nishikawa et al. | 250/363 S |
| 4,228,515 | 10/1980 | Genna et al. | 250/366 |

*Primary Examiner*—Janice A. Howell
*Attorney, Agent, or Firm*—Sandler & Greenblum

[57] ABSTRACT

A map of a radiation field produced by a gamma camera is corrected for three types of spatially dependent errors in a manner that corrects for each error independently of the others. The errors corrected for are dislocations which result from the non-linearity of the optics, photomultipliers and electronics of the camera, energy window variations resulting from inhomogeneity of the optical system which includes the crystal, light guide, and photomultipliers, and the non-uniform sensitivity of the head resulting from the non-uniform stopping power of the crystal and collimator of the camera head. The map is corrected by obtaining a set of correction factors associated with each type of error using a calibration technique that insures independence between the various correction factors, and applying the correction factors to the map obtained in a nuclear imaging process in a way that independently corrects the map for each type of error.

11 Claims, 10 Drawing Figures

GAMMA CAMERA CORRECTION SYSTEM AND METHOD FOR USING THE SAME

This is a continuation of application Ser. No. 161,050 filed June 19, 1980, now U.S. Pat. No. 4,424,446.

TECHNICAL FIELD

The invention relates to a correction system for a gamma camera and to a method for using the same.

BACKGROUND OF THE INVENTION

The head of a conventional gamma camera comprises a collimator for receiving radiation stimuli from a radiation field, a scintillation crystal which produces light events at spatial locations corresponding to the locations at which stimuli passing through the collimator interact with the crystal, and an optical system for transmitting light produced by the light events to an array of photomultipliers. Each photomultiplier produces an output signal that depends on the spatial location of the event in the crystal relative to the photomultiplier; and these output signals are applied to signal processing equipment which calculates the x, y coordinates of an event based on assigning different weights to the output signals of the photomultipliers according to their location in the array.

An event can be recorded by using the calculated coordinates to control the deflection of a CRT whose intensity control gates on the beam for a predetermined short period of time if the total energy of the light event lies within a predetermined energy window as determined by a single channel analyzer. In such case, a brief flash of light appears on the screen at the calculated coordinates of each event; and a film exposed to light from the screen for a predetermined period of time will provide a record of the intensity distribution of the radiation field by recording the light events as gray-scale variations in the film.

In other systems, events can be recorded in a digital memory having a register associated with each picture element of the field of view of the camera. In this case, the occurrence of an event at a given calculated x, y coordinate location is recorded by indexing the memory register at the address corresponding to the coordinates of the light event. After accumulating counts for a given time interval, an image of the radiation field is produced by displaying the contents of the memory registers on a CRT, the brightness of a picture element of the display being directly related to the contents of the corresponding memory register.

Whichever approach is used to produce an image of a radiation field, the quality of this image is determined by the resolving power of the camera and its sensitivity or homogeneity. The resolving power of a camera is its ability to distinguish between stimuli originating in adjacent locations in a radiation field, and is determined mainly by the optical system of the camera. The sensitivity of a gamma camera, on the other hand, is concerned with the uniformity of the response of a camera to a uniform distribution of stimuli over the active area of the crystal. The present invention is concerned with improving the sensitivity of a gamma camera rather than improving its resolution. As is well known in the art, an image produced by flooding an uncompensated gamma camera with a uniform radiation field will produce a variegated pattern whose brighter regions closely match the photomultiplier array. Particularly in a nuclear medicine environment, this inhomogeneous response to a uniform radiation field, if uncompensated, will reduce the accuracy of fidelity of an image of an unknown non-uniform field such as is produced by a human patient into whom a radioactive pharmaceutical is injected.

An important contribution to the inhomogeneity or variation in sensitivity of a gamma camera is the dislocation or distortion of the image due to deviations from linearity of the responses of the photomultipliers of the camera head. The response of an individual photomultiplier across its photosensitive surface is non-linear, and in fact, is quasi-Gaussian in nature; and it is conventional to manipulate the outputs of the photomultipliers by weighting them such that, as a group, the photomultipliers have a substantially linear response. Nevertheless, the overall response of the photomultipliers is not exactly linear with the result that the calculated coordinates of an event will be displaced from the actual coordinates of an event. Furthermore, the displacement of the calculated position from the true position of an event is spatially dependent.

Dislocation or distortion of a gamma camera image can be compensated for by following the technique disclosed in U.S. Pat. No. 3,745,345 (whose disclosure is hereby incorporated by reference). In such technique, a given camera is calibrated before being used for imaging a patient by interposing a pierced shield between the crystal and a uniform radiation field. The locations of the holes in the shield are precisely known so that the coordinates of a given hole can be compared with the first moment of the distribution of counts associated with the given hole as calculated by the signal processing equipment of the camera. The process is repeated after shifting the shield and until a 2-dimensional dislocation map of the desired density of points over the entire crystal is created, each entry in the map being the correction factor which must be applied to the calculated coordinates of an event (from which a distorted image of the radiation field can be constructed) in order to relocate the events and provide a less distorted image. The dislocation correction factors are thus predetermined in accordance with deviations from linearity of the photomultipliers to stimuli that interact with the head. Once such a map of dislocation factors is obtained, the calibration mode is terminated and the camera is used for imaging a patient for a period of time during which it is assumed that the dislocation process remains constant.

The dislocation map can be used to correct the image on an event-by-event basis (i.e., looking up the correction factor for each event as it occurs and relocating it for storage at its corrected location rather than its distorted location), or corrections can be done after a complete, albeit distorted, image is obtained. In the latter case, correction factors are applied to the counts in each picture element of a digital memory map of the distorted image according to the contents of the dislocation map.

Another significant contribution to the inhomogeneity of a gamma camera arises from the spatial dependence of the so called Z-signal of a gamma camera. As discussed in U.S. Pat. No. 4,095,108 (whose disclosure is hereby incorporated by a reference), the amount of light received by the photosensitive surfaces of all the photomultipliers of an array in a camera due to a given interaction of a radiation stimulus of fixed energy with the crystal, is a function of the position of the light event in the crystal. The spatial dependence of the total energy of a light event can be taken into account by a so-called Z-signal correction map which tabulates the spatial dependence of deviations in total energy of events due to inhomogeniety of the optical system which includes the crystal light guide and photomultipliers. If the total energy of the event lies inside the energy window determined by the Z-correction map at the calculated coordinates of the event, then the event is "counted" by indexing a counter in a digital memory at an address corresponding to the calculated coordinates of the event.

As in the case of distortion correction, Z-signal correction improves image quality over a non-compensated gamma camera; and the image quality is greatly improved if both dislocation and Z-signal compensations are utilized.

Neither of these techniques for improving image quality of a gamma camera, however, takes into account the inherent mechanical imperfections of a camera such as the non-uniform stopping power of a crystal, or differences in the geometry of the many openings in the collimator. The stopping power of a crystal or of the collimator relates to the ability of a target receiving stimuli to interact with the stimuli. The stopping power is generally expressed in terms of the ratio of the number of particles that interact with a target to the number of particles incident on the target. As indicated above, both the crystal and the collimator are likely to have spatially dependent stopping powers, no matter how well they are constructed. Thus, correction for distortion or Z-signal inhomogeneity will not eliminate image distortions due to inherent mechanical imperfections in the camera components.

In an effort to provide compensation simultaneously for all three factors affecting the inhomogeneity of a gamma camera, it is conventional to provide what is termed a "flood correction" in which a camera is flooded with a uniform radiation field and the resulting image is used to construct a "flood map". Because the input stimuli at each elemental area of the crystal is known to be constant, deviation in the brightness of an elemental area of the image from the average brightness of the entire image permits a correction factor to be calculated which can be applied to a map produced by a gamma camera in normal usage. The correction factors over the entire crystal can be stored in a digital map and called up to correct the raw data obtained by the camera. For example, if a given picture element is say 10% darker than the average brightness of the image obtained under flood conditions, the number of counts recorded in this picture element under imaging conditions would be increased by 10%. While this technique provides a simple approach to image correction, and often provides improved results, it is not a sound approach to image correction.

The inherent deficiency in this technique is illustrated by assuming the given picture element images an element of a radiation field where there is actually a low level of stimuli emitted in comparison to an adjacent region. With the conventional flood correction, the counts accumulated in this picture element would be increased by 10% thus concealing the actual situation. Such a display of image portions that are not actually present in the object being imaged is termed an artifact; and the presence of artifacts in gamma camera images is highly undesirable for obvious reasons.

Therefore, an object of the present invention to provide a new and improved gamma camera correction circuit and a method for using the same wherein the resulting image is improved over the image obtained with conventional correction techniques.

DISCLOSURE OF INVENTION

Briefly summarizing the present invention, a map of a radiation field produced by a gamma camera is corrected for three types of spatially dependent errors in a manner that corrects for each error essentially independently of the others. The errors corrected for are dislocations which result from the non-linearity of the optics, photomultipliers and electronics of the camera, energy window variations resulting from inhomogeneity of the optical system which includes the crystal, light guide, and photomultipliers, and non-uniform sensitivity of the head resulting from the non-uniform stopping power of the crystal and collimator of the camera head. The map is corrected by obtaining a set of correction factors associated with each type of error using a calibration technique that ensures substantial independence between the various correction factors, and applying the correction factors to the map obtained in a nuclear energy process in a way that substantially independently corrects the map for each type of error.

In the preferred technique, calibration is carried out in two steps, the first one resulting in obtaining the dislocation correction factors and the energy window correction factors using a perforated plate interposed between the collimator of the camera and a flood source. Each set of correction factors is thus a function of distorted coordinates for events produced by the gamma camera, and is stored in a map for use in the second calibration step. In the second step, the perforated plate is removed and the data obtained from the flood source are corrected by the dislocation and energy window correction factors to relocate each event. Only after the relocated map of the flood source is obtained are the sensitivity correction factors computed in a way that will reproduce the uniform flood field. As a consequence, the sensitivity correction factors are substantially isolated from errors due to the non-linearity of the optics, photomultipliers and electronics of the camera, from energy window variations resulting from inhomogeneity of the optical system which includes the crystal, light guide, and photomultipliers, and from non-uniform sensitivity of the head due to non-uniform response of the crystal and collimator.

Once the sensitivity correction factors are computed, they are used in a nuclear imaging process only in connection with data previously corrected for dislocation and energy window variations. In other words, upon completion of the calibration process, nuclear imaging can be carried out in a conventional way to obtain a map based on distorted coordinates. Because the dislocation and energy window correction factors are available as functions of distorted coordinates, these two sets of factors are first applied to the distorted data to relocate the events into what is termed relocated data. Thereafter, the sensitivity correction factors, which are functions of relocated coordinates, are applied to the relocated data to produce an undistorted map that represents data substantially independently corrected for all three types of errors.

BRIEF DESCRIPTION OF DRAWINGS

Embodiments of the present invention are illustrated in the accompanying drawings wherein.

BEST MODE FOR CARRYING OUT THE INVENTION

Figure 1:
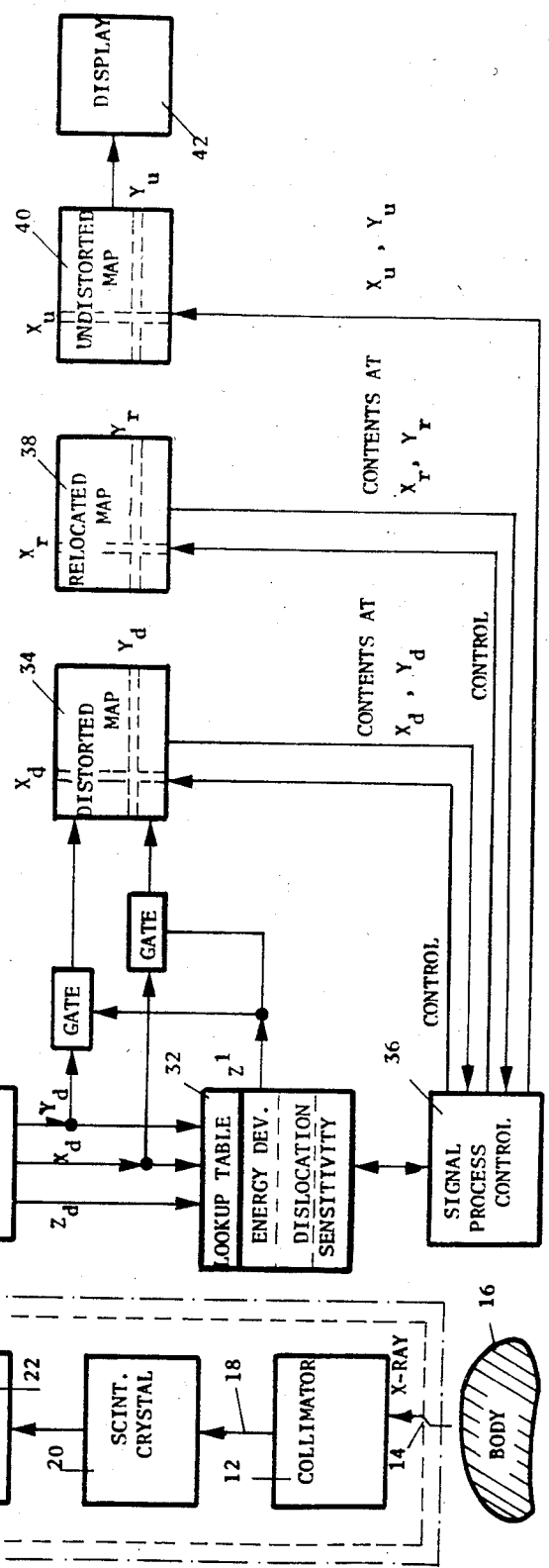
FIG. 1 is a block diagram of a gamma camera showing the gamma camera head and electronic circuitry associated with the head for carrying out the present invention.

Referring now to FIG. 1, reference numeral 10 designates the head of gamma camera 11 comprising collimator 12 for receiving radiation stimuli 14 from a radiation field 16 and passing only those stimuli 18 having a predetermined direction to scintillation crystal 20 which produces light events at spatial locations corresponding to the locations at which the stimuli interact with the crystal; and optical system 22 for transmitting light produced by the light events to an array of photomultipliers 24. Each photomultiplier produces an output signal that depends on the spatial location of the event in the crystal relative to the photomultiplier. Gamma camera head 10 is totally conventional in nature and is well-known to those skilled in the art.

Associated with head 10 is gamma camera signal processing equipment 26 which includes a single channel analyzer (SCA) with a relatively wide window and which receives the output signals produced by the photomultiplier array. All of the outputs of the photomultipliers are added together to form the so-called Z signal, which is a measure of the total energy of a light event. If the Z signal lies within the energy window of the SCA, it is assumed that the event arose because of the interaction of a primary stimulus emitted by the radiation field 16. In such case, the coordinates X, Y of the event are calculated in a known manner and applied to A/D converter 30, which converts the analog signals produced by the computation circuitry to digital signals for further processing.

The digital coordinates X, Y are applied to lookup table 32 which contains three sets of correction factors, namely the energy window correction factors, the dislocation correction factors, and the sensitivity correction factors obtained by a calibration process described below wherein the energy window and dislocation correction factors are each based on distorted space. Thus, a triad of correction factors is contained in table 32 for each picture element of the image to be reproduced by the gamma camera. This triad of correction factors is extracted from the table and is used in the manner indicated below. If the Z signal produced by converter 30 lies within the window defined by the energy window correction factor, validation signal Z' is produced which gates the coordinates X, Y into a digital storage medium which is identified as distorted map 34 where a register at the address specified by the coordinates is indexed thereby recording an indication that an event has occurred at the coordinates X, Y. The energy window correction factor provides assurance that the event was caused by a primary stimulus arising from radiation field 16.

In the preferred embodiment, distorted map 34 is completed before any further correction factors are applied. Thus, after a period of time long enough for a sufficient number of events to have been detected in crystal 20, distorted map 34 will be completed. This map will have to be corrected, however, for dislocation and sensitivity distortions. The first step in this correction process is for signal process control 36 to apply the set of dislocation correction factors to the respective contents of each elemental area of distorted map 34. Thus, signal process control 36 withdraws the contents of a given elemental area of the distorted map and, at the coordinates of such elemental area, the dislocation correction factor is obtained from lookup table 32. With this correction factor in hand, control 36 will make the necessary correction as disclosed in U.S. Pat. No. 3,745,345, and relocate the contents in relocated map 38. After the entire distorted map is relocated into relocated map 38, control 36 can then carry out the sensitivity correction. This is done by applying the set of sensitivity correction factors from table 32 to the respective contents of each elemental area of the relocated map in order to obtain an undistorted map of the radiation field. The undistorted map is contained in memory storage 40. When this undistorted map is completed, an undistorted display of the radiation field can be produced on display 42. Such display will have been corrected for distortions due to non-linearity of the response of the photomultipliers to stimuli interacting with the crystal (i.e., dislocations), for distortions due to deviations in peak value of the total energy of the events (i.e., energy window variations), and for distortions due to non-uniformity in the stopping power of the camera head. Furthermore, the corrections will have been carried out in a way that substantially independently corrects these distortions.

Instead of completing map 34 before creating the relocated map and the undistorted map, the corrections can be carried out on-the-fly on an event-by-event basis. That is to say, if the calculated coordinates X, Y are validated by signal Z', then the correction factors associated with the coordinates X, Y can be obtained from lookup table 32 and the corrections will be applied directly to the event. In such case, the event or a number representing the event would be stored in undistorted map 40. When this map is completed, its contents could be displayed at 42.

Figure 2:
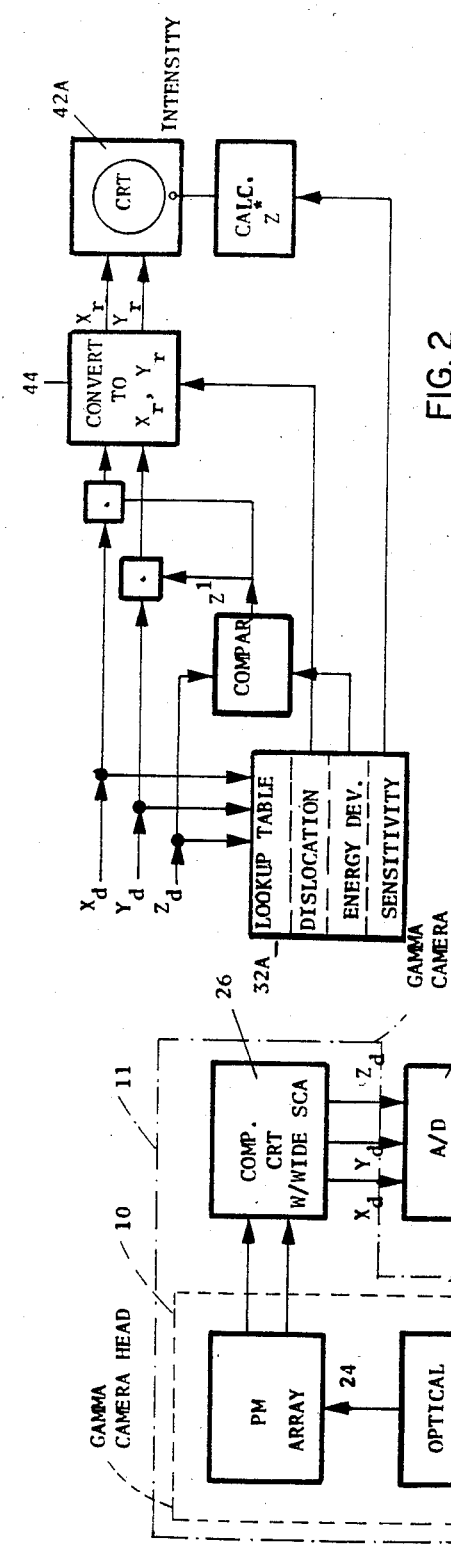
FIG. 2 shows an analog technique for storing an image.

FIG. 2 shows an alternate arrangement for displaying an image of radiation field 16 using a CRT. In this instance, the energy signal produced by computer computation circuitry 28 as well as the calculated coordinates are applied to lookup table 32A. If the total energy signal lies within the spatially dependent window determined by the coordinates X, Y, then validation signal Z' will be developed. The coordinates calculated by computation circuitry 28 are then passed to converter 44 which operates on the coordinates X, Y with the dislocation correction factor (as determined by the coordinates) thereby relocating the event to relocated coordinates. The relocated coordinates are applied to the deflection controls of CRT 42A so that a light spot appears on the face of a CRT at the relocated coordinates. The intensity control of the CRT display is derived from the sensitivity correction factor from which an intensity level $Z^*$ can be computed. The latter signal is applied to the intensity control with the result that the amount of light emitted by the spot on the screen of CRT is modulated in accordance with the sensitivity correction factor.

Figure 3:
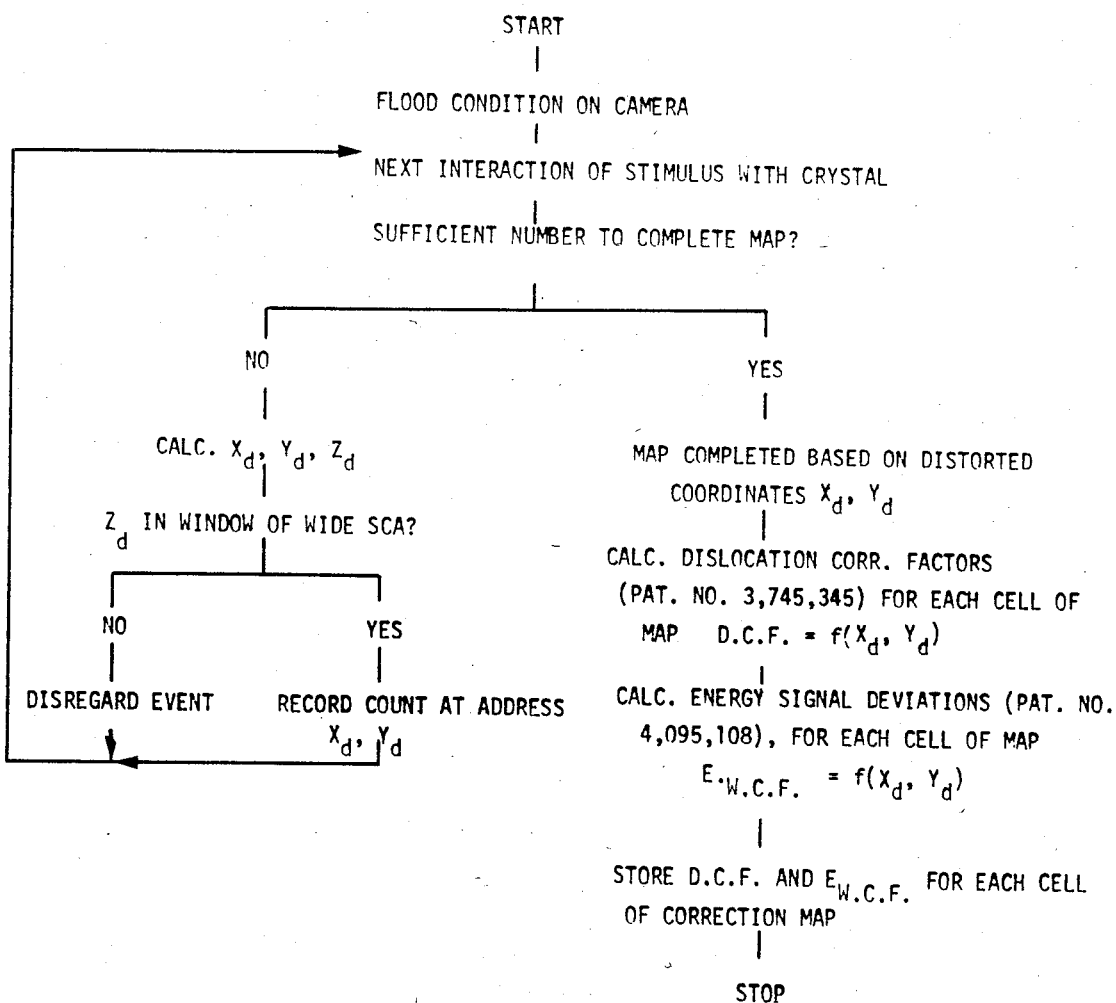
FIG. 3 is a flow chart showing the initial steps of a first mode of calibration.
Figure 4:
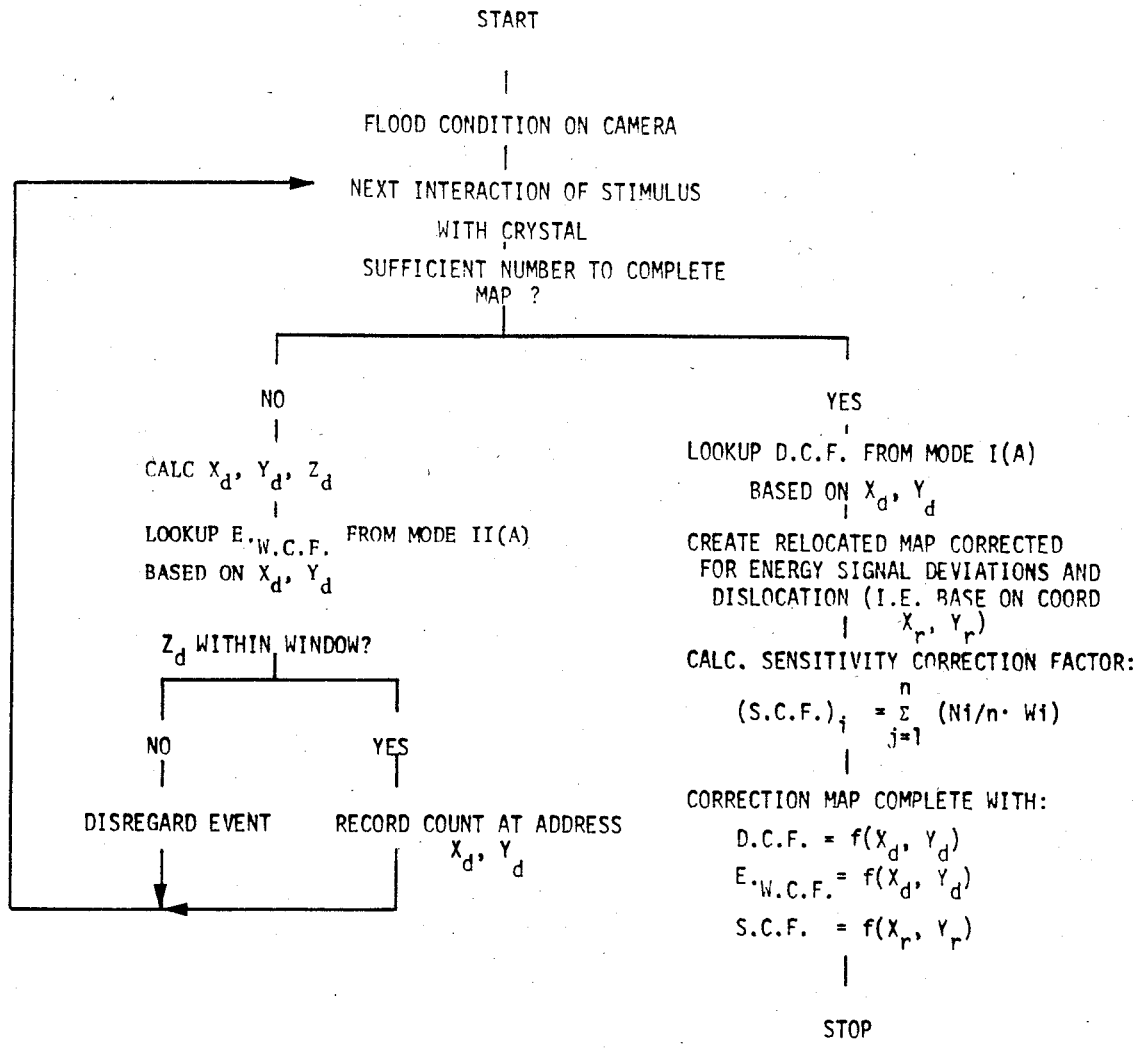
FIG. 4 is a flow chart showing the final steps of the first mode of calibration.

A first calibration mode for obtaining the correction factors is illustrated in FIGS. 3 and 4. As seen in FIG. 3, the distortion correction factors and the energy window correction factors are obtained in accordance with the teachings in U.S. Pat. No. 3,745,345 and U.S. Pat. No. 4,095,105, respectively. Specifically, the flow chart indicated in FIG. 3 is somewhat schematic in that the stimuli passing through the holes in the perforated metal plate occur randomly in time during the calculation process with the result that the chart is not entirely accurate in describing a time sequence of events, but is helpful in explaining the calibration procedure. In any event, the calibration process is begun by providing a uniform source of radiation and placing a perforated plate between the source and the collimator. When a stimulus ineracts with the crystal, the coordinates and the total energy of the event are calculated. If the total energy lies within the window of a wide SCA, a count is stored in a distorted map at the address of the event. If the total energy of the event lies outside the window of the SCA, then the event is discarded and the computation of the coordinates of the next light event is carried out. After a sufficient number of events will have occurred, a distorted map of the flood source as seen through the plate will be obtained. Based on the disclosure in U.S. Pat. No. 3,745,345, the dislocation correction factors are calculated for each cell of the map. These correction factors are thus a function of distorted coordinates.

Following the teaching in U.S. Pat. No. 4,095,108, the energy signal deviations are calculated for each cell of the map; and the energy window correction factors computed. These also will be a function of the distorted coordinates. Each of the correction factors so computed is stored in a cell of a lookup table as indicated in FIG. 1. This completes the initial steps of the calibration mode; and the final steps of the mode (see FIG. 4) are carried out to obtain the sensitivity correction factors. After the perforated plate is removed, the camera is again flooded with a uniform source. In this instance, the gamma camera computes the coordinates and the total energy signal; but the total energy signal is now tested using the energy window correction factors obtained from the first mentioned calibration mode. As indicated above, the energy window correction factors are based on distorted coordinates which are the type of coordinates available here. If the total energy lies within the energy window so obtained, then a count is recorded at the address specified by the calculated coordinates (i.e., distorted). Otherwise, the event is ignored and the next event enters the system for computation purposes.

After a number of events have occurred sufficient to permit a complete map of the flood source to be obtained, the resulting map is corrected using the distortion correction factors obtained from the previous calibration mode. As a result, events in distorted space are relocated in another map (i.e., relocated space) which will be the flood condition map corrected for both energy signal deviations and dislocation. From this relocated map, the sensitivity correction factors for each elemental area of the map are computed. In order to compute the sensitivity correction factor for a given elemental area of the relocated map, the computation indicated in FIG. 4 can be carried out. Specifically, the sensitivity correction factor for a given area is obtained by dividing the total number of events in the map by the product of the number of elemental areas and the number of events in the given elemental area. That is to say, the sensitivity correction factor of a given area is actually the ratio of the average number of events in the elemental areas of the relocated map to the actual number of events in the given elemental area. Multiplying the actual number of events in a given area by the correction factor for such area will thus yield the average number of events, a quantity, by definition, that is the same for each area.

When the calibration mode is completed, it can be seen that a lookup table will have been developed having three entries for each elemental area, namely, a dislocation correction factor which is a function of distorted coordinates, an energy window correction factor which is also a function of distorted coordinates, and a sensitivity correction factor which is a function of relocated coordinates. This means that in carrying out an actual nuclear imaging process, it will be necessary to correct the distorted data obtained from the gamma camera for both dislocation and the energy window variations before making the sensitivity correction.

Figure 5:
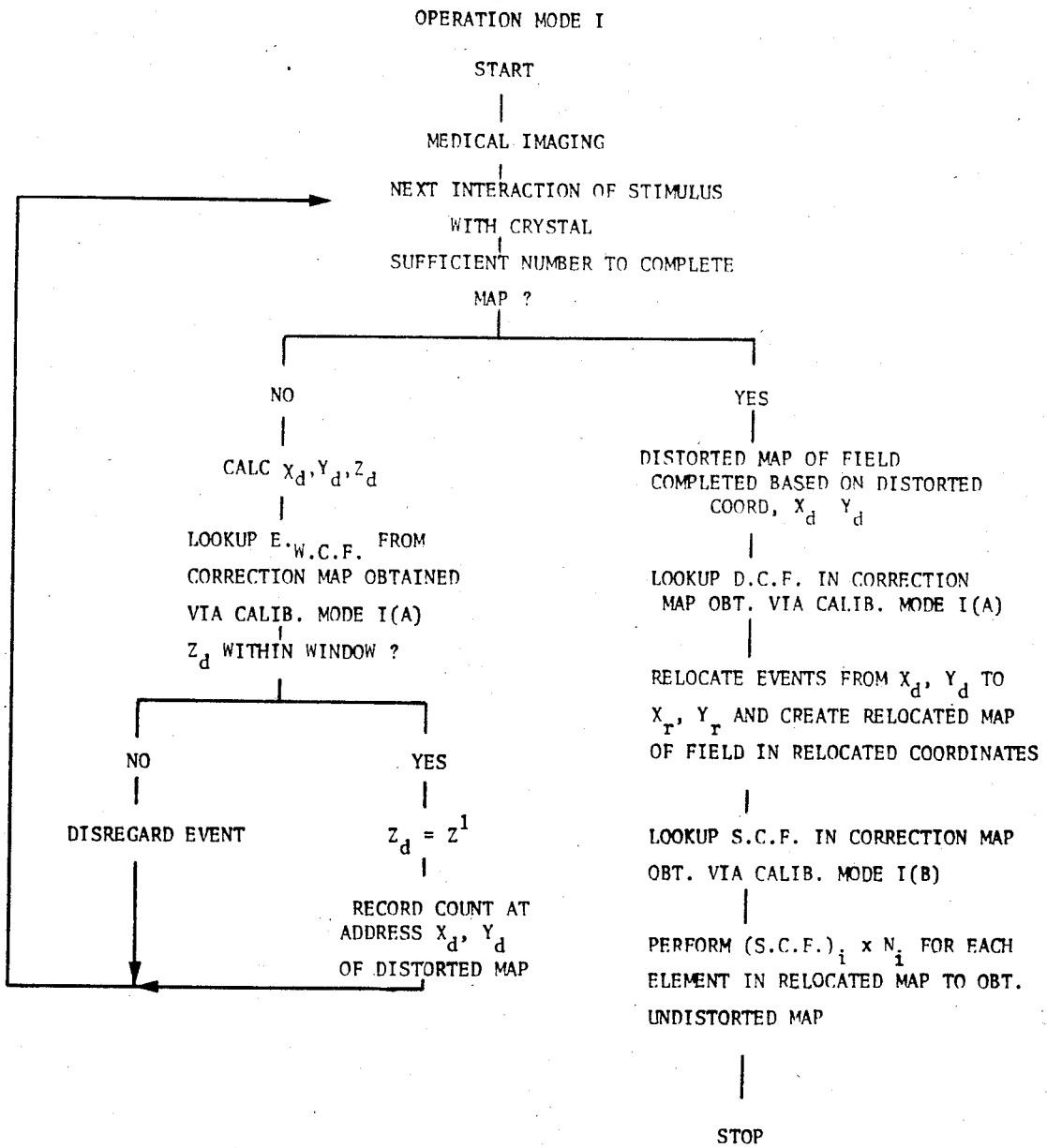
FIG. 5 is a flow chart showing an operational mode utilizing the first mode of calibration.

This situation is shown in FIG. 5 where a medical imaging process is illustrated. Specifically, after an interaction with the crystal is detected, the distorted coordinates are computed as is the total energy. Using the distorted coordinates, the energy window correction factor can be looked up for the purpose of determining whether the total energy of the event lies within a spatially dependent window. In the event that the total energy lies outside the window, the event is disregarded and the coordinates of the next event detected by the crystal are computed. However, if the total energy does lie within the energy window established by the energy window correction factor, then a validation signal is produced and a register, at the address specified by the calculated coordinates, is indexed in a digital memory matrix.

After a sufficient number of events have occurred to permit a complete map in distorted space to be obtained, the imaging process is terminated. Offline, the events in the distorted map are relocated in a relocated map by using the distortion correction factors. After relocation has been completed, the sensitivity correction factors are looked up in the table and applied to the relocated map. Specifically, the contents of a given elemental area of the relocated map are multiplied by the sensitivity correction factor for the elemental area thereby obtaining an undistorted map.

Figure 6:
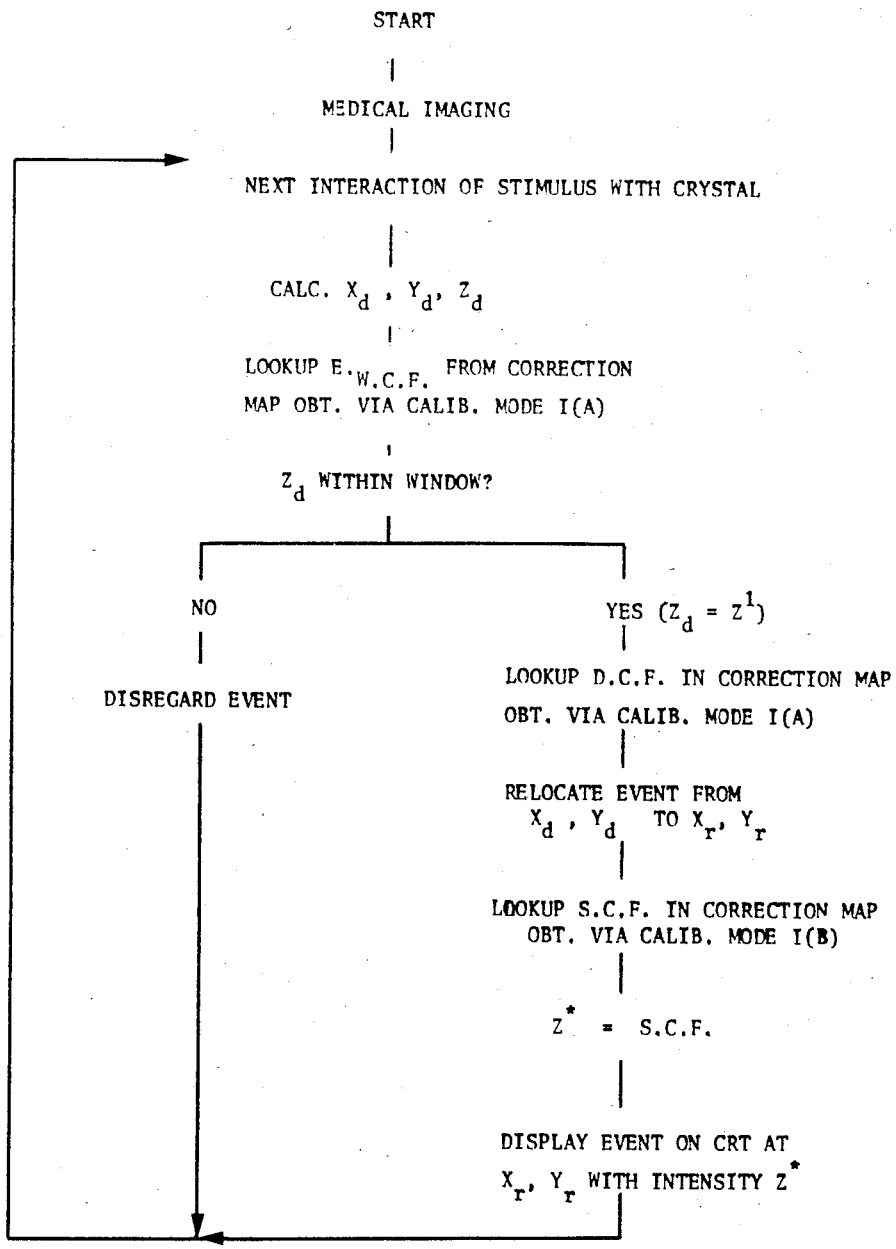
FIG. 6 is a flow chart showing an alternative mode of operation using the first calibration mode.

In the event that an operational mode is desired where the correction is to be made on an event-by-event basis rather than making the correction on a completed map, FIG. 6 shows the procedure that can be followed. In this case, the distortion correction factor is looked up in the lookup table only if the total energy of the event lies within an energy window determined in accordance with the energy window correction factor based on the distorted coordinates of the event. This permits the event to be relocated and permits the sensitivity correction factor to be applied in order to compute a Z*. The event can then be displayed on the CRT as indicated in FIG. 2.

Figure 7:
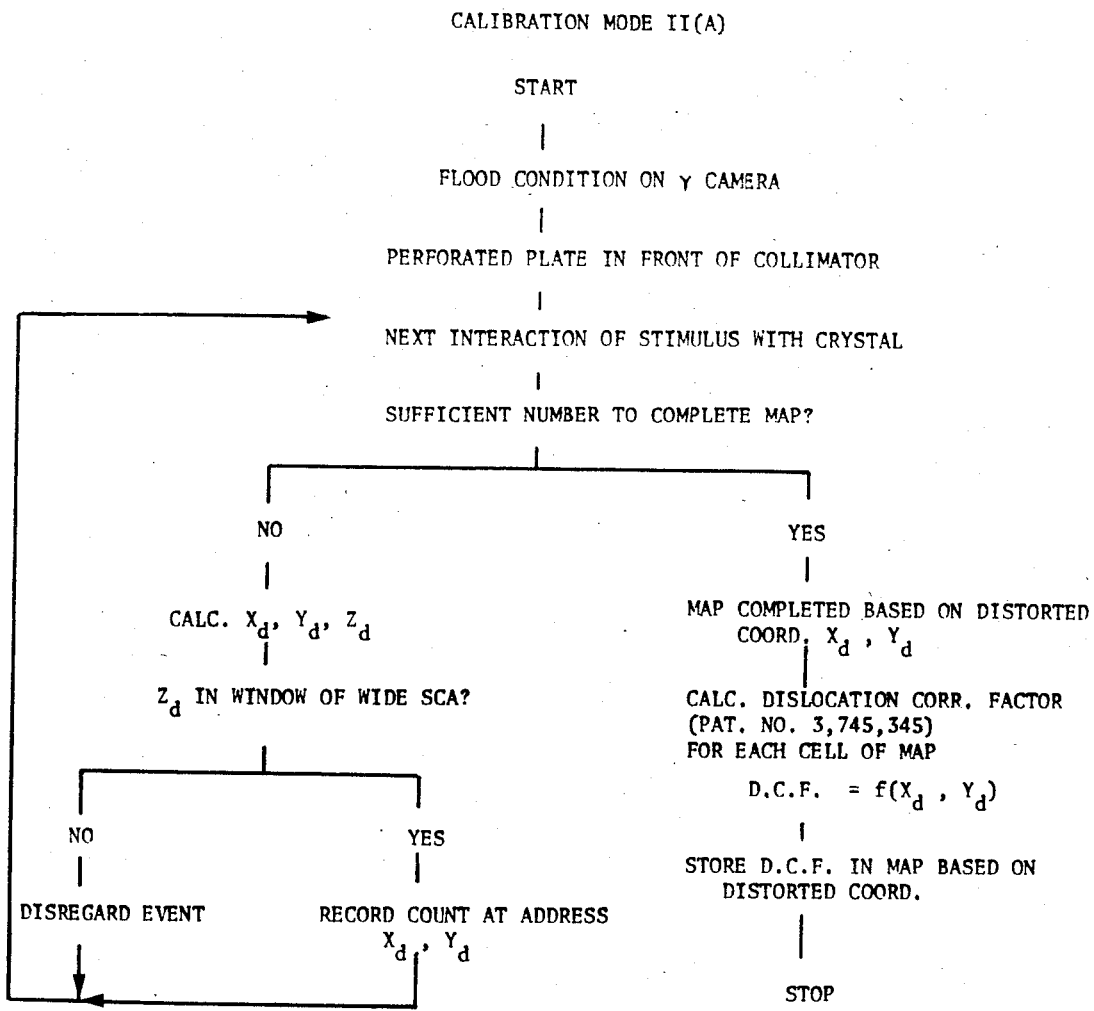
FIG. 7 is a flow chart showing the initial steps of a second mode of calibration.
Figure 8:
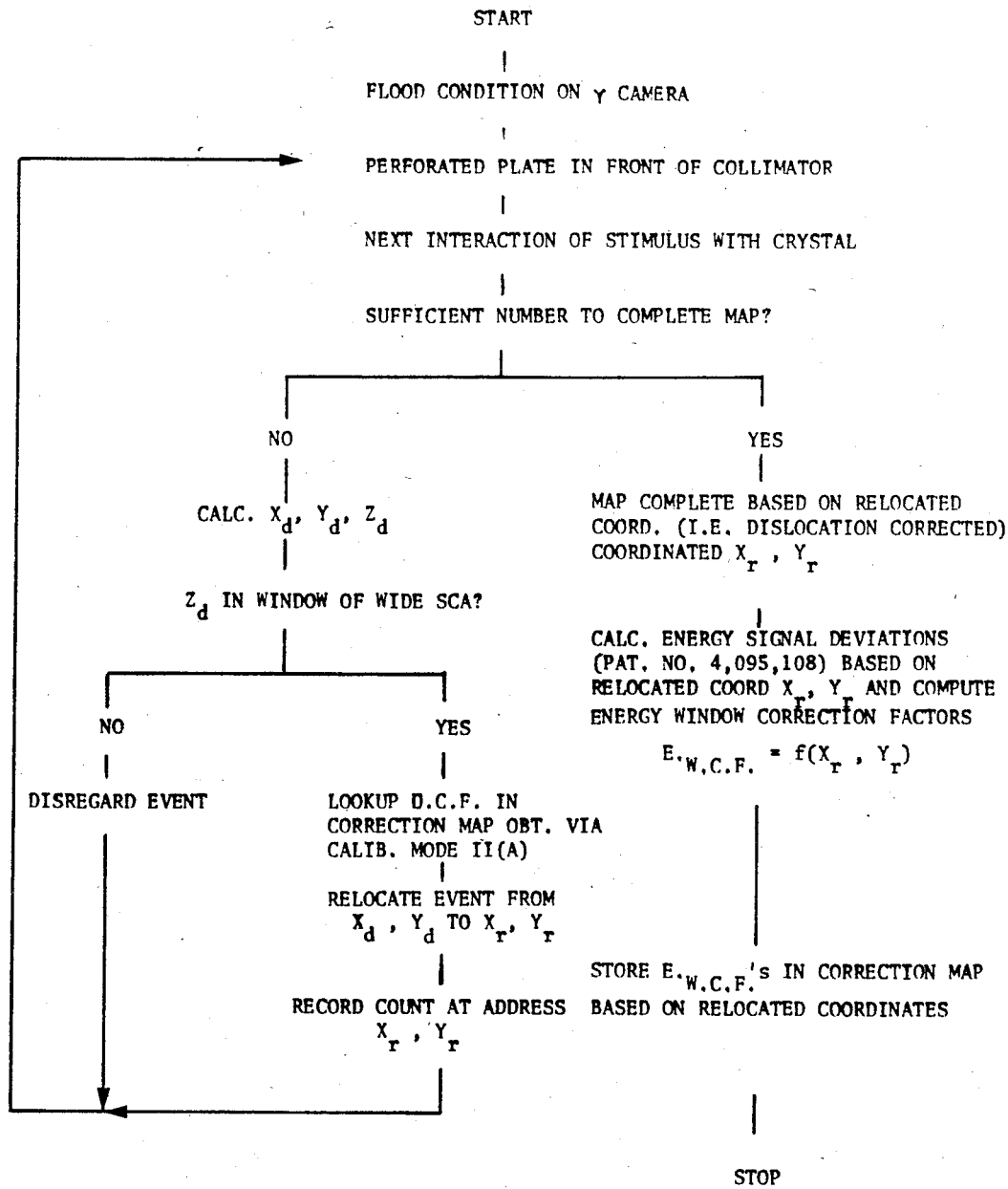
FIG. 8 is a flow chart showing the intermediate steps of the second mode of calibration.
Figure 9:
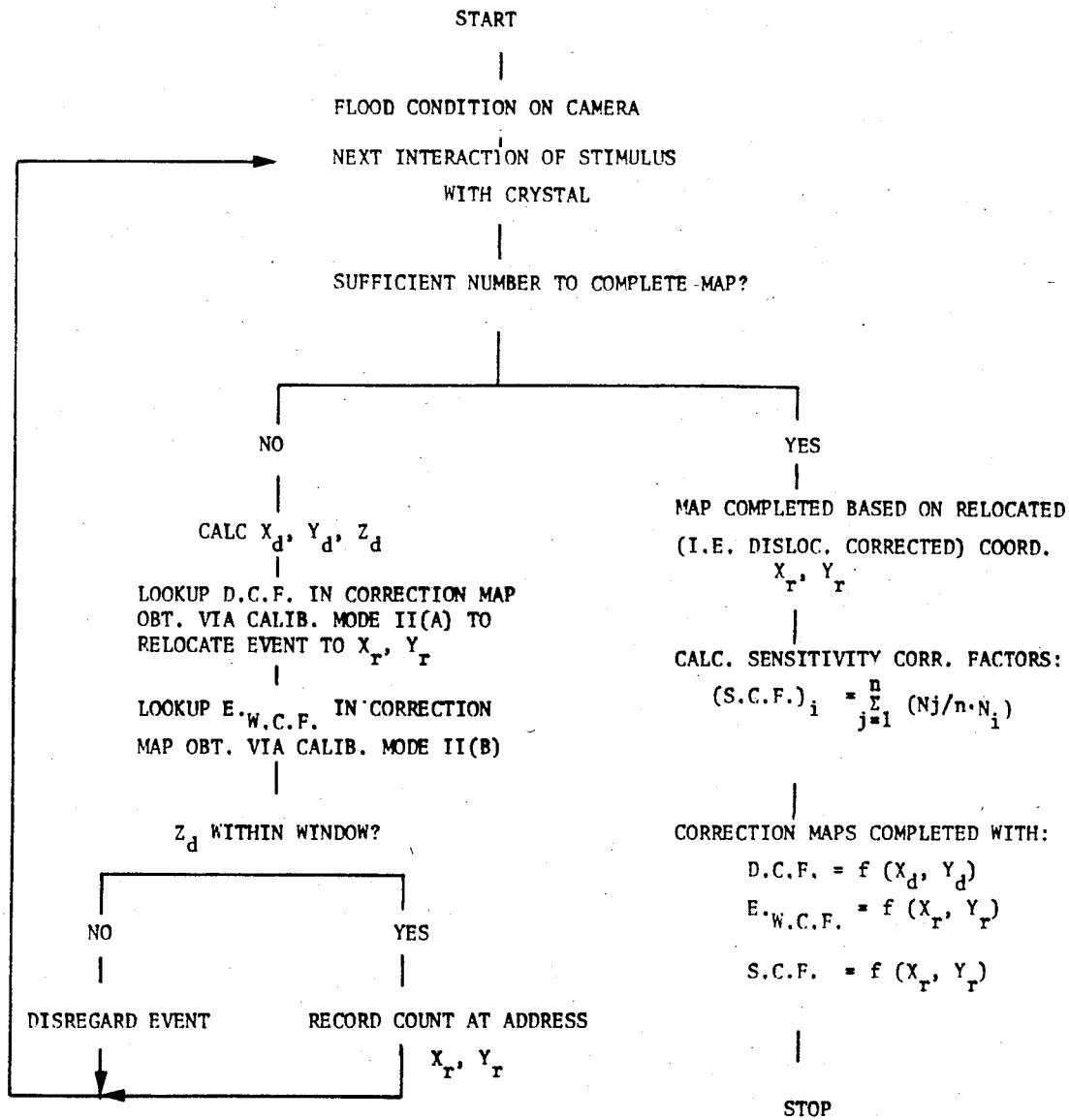
FIG. 9 is a flow chart showing the final steps of a second mode of calibration.

As an alternative to the first calibration mode described above, a second calibration mode indicated in FIGS. 7–9 can be carried out. In this mode, three separate steps are required, each step computing a different correction factor. The first correction factor computed is the dislocation correction factor based on the distorted coordinates. The second correction factor is the energy window correction factor but this correction factor is based on relocating each event on an event-by-event basis by using the distortion correction factor previously obtained. As a consequence, the energy window correction factors are based on relocated space rather than distorted space as was the case with the first calibration mode. The last correction factor is obtained by using the procedure shown in FIG. 9 wherein both the distortion correction factor and the energy window correction factor are applied to each event, as the event occurs, for producing a relocated map. When this map is completed the sensitivity correction factor can be computed. In this instance, the dislocation correction factor will be a function of the distorted coordinates while the energy window correction factor and the sensitivity correction factor are each functions of the relocated coordinates.

Figure 10:
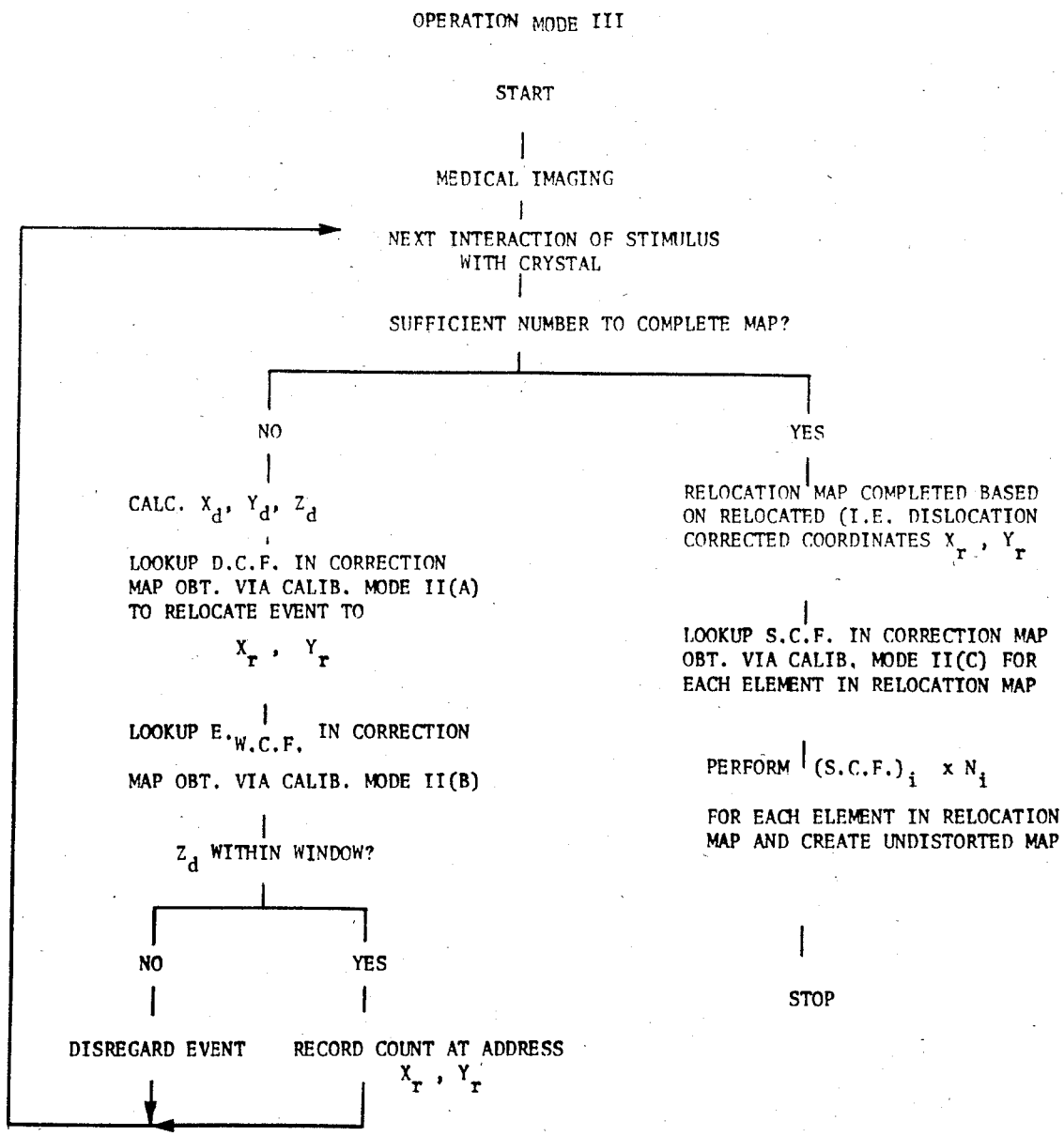
FIG. 10 is a flow chart showing an operational mode utilizing the second calibration mode.

FIG. 10 shows the operational mode of a device where the calibration is carried out in accordance with FIGS. 7–9. In this case, the coordinates and the total energy of each event are computed and the dislocation correction factor is obtained from a lookup table thereby relocating the event. When the event has been relocated, the energy window correction factor can be looked up and applied to thereby determine whether or not the total energy at the relocated location of the event is within the proper energy window. If this is the case, then an index register in a relocation map is indexed; otherwise the event is disregarded. When a sufficient number of events have occurred to complete the relocation map, the medical imaging process is terminated. Offline, the sensitivity correction factors can be applied in the manner indicated above to obtain an undistorted map.

It is believed that the advantages and improved results furnished by the method and apparatus of the present invention are apparent from the foregoing description of the preferred embodiment of the invention. Various changes and modifications may be made without departing from the spirit and scope of the invention as described in the claims that follow.

We claim:
1. A gamma camera comprising:
(a) a detector head that includes a plurality of photodetectors for producing output signals in response to radiation stimuli which are emitted by a radiation field and which interact with the detector head and produce an event;
(b) signal processing circuitry responsive to the output signals of the photodetectors for producing a sum signal that is a measure of the total energy of the event;
(c) an energy discriminator having a relatively wide window for comparison with the sum signal;
(d) said signal processing circuitry including coordinate computation circuitry for operating on said output signals, and calculating an X,Y coordinate of an event when said sum signal lies within the window of said energy discriminator;
(e) an energy correction table containing spatially dependent energy windows for producing a validation signal if the total energy of an event lies within the window associated with the X, Y coordinates of the event;
(f) said signal processing circuitry including a dislocation correction table containing spatially dependent correction factors for converting the X,Y coordinates of an event to relocated coordinates in accordance with correction factors determined by said X,Y coordinates;
(g) a digital memory for storing a map of the radiation field; and
(h) means for recording an event at its relocated coordinates in the memory if the energy correction table produces a validation signal.

2. A gamma camera according to claim 1 including:
(a) a sensitivity correction table containing a set of spatially dependent correction factors; and
(b) means for applying said set of correction factors to the respective contents of each elemental area of said map in order to obtain an undistorted map of the radiation field.

3. A gamma camera comprising:
(a) a detector head that includes a plurality of photodetectors for producing output signals in response to radiation stimuli which are emitted by a radiation field and which interact with the detector head and produces an event;
(b) signal processing means responsive to said output signals for calculating X,Y coordinates of and event;
(c) a digital memory for saving a map of the radiation field;
(d) at least two sets of independent, spatially dependent correction factors;
(e) means for obtaining a correction factor from each of said two sets in accordance with the calculated X,Y coordinates of an event; and
(f) means sequentially utilizing the obtained correction factors on an event-by-event basis, in real time, for recording said map of the radiation field in the digital memory;
(g) said signal processing means calculates an energy signal proportional to the total energy of an event and one set of said at least two sets of correction factors are energy windows, and the camera includes means for comparing the total energy of an event with the energy window associated with the calculated coordinates; and
(h) wherein another set of said at least two sets of correction factors are dislocation correction factors for relocating the X,Y coordinates of an event to relocated coordinates in accordance with a correction factor from said another set of at least two sets of correction factors determined by the calculated X,Y coordinates of an event.

4. A nuclear imaging device comprising:
(a) a head that includes a plurality of photodetectors for producing output signals in response to radiation stimuli which are emitted by a radiation field and interact with the device;

(b) coordinate computation circuitry for operating on said signals and producing, for an interaction, a pair of calculated coordinate signals that define distorted coordinates of the interaction;

(c) means for storing spatially dependent dislocation correction factors;

(d) means for storing spatially dependent energy window correction factors;

(e) means responsive to an occurrence of an interaction for producing a validating signal validating the interaction if the total energy thereof satisfies the energy window correction factor evaluated at the calculated coordinates of the interaction; and (f) means for converting the calculated coordinates of a validated interaction into relocated coordinates by applying to the calculated coordinates the dislocation correction factor evaluated at the calculated coordinates.

5. A nuclear imaging device comprising:

(a) a head that includes a plurality of photodetectors for producing output signals in response to radiation stimuli which are emitted by a radiation field and interact with the device;

(b) coordinate computation circuitry for operating on said signals and producing, for an interaction, a pair of calculated coordinate signals that define distorted coordinates of the interaction;

(c) means for storing spatially dependent dislocation correction factors;

(d) means for storing spatially dependent sensitivity correction factors based on a relocated coordinate system;

(e) means for converting the calculated coordinates of an interaction into relocated coordinates by applying to the calculated coordinates the dislocation correction factor evaluated at the calculated coordinates; and (f) means for converting the relocated coordinates of an interaction into undistorted coordinates by applying to the relocated coordinates the sensitivity correction factor evaluated at the relocated coordinates of a validated interaction.

6. A nuclear imaging device comprising:

(a) a head that includes a plurality of photodetectors for producing output signals in response to radiation stimuli which are emitted by a radiation field and interact with the device;

(b) coordinate computation circuitry for operating on said signals and producing, for an interaction, a pair of calculated coordinate signals that define distorted coordinates of the interaction;

(c) means for storing spatially dependent energy window correction factors;

(d) means for storing spatially dependent sensitivity correction factors based on a relocated coordinate system;

(e) means responsive to the occurrence of an interaction for producing a validating signal validating the interaction if the total energy thereof satisfies the energy window correction factor evaluated at the calculated coordinates of the interaction; and (f) means for converting the calculated coordinates of a validated interaction into undistorted coordinates by applying to the calculated coordinates the sensitivity correction factor evaluated at the relocated coordinates of the validated interaction.

7. A nuclear imaging device, comprising: a head that includes a plurality of photodetectors for producing output signals in response to radiation stimuli which are emitted by a radiation field and interact with the device; coordinate computation circuitry responsive to said signals for measuring total energy of an interaction and producing a pair of calculated coordinate signals for each interaction in which the measured total energy exceeds a threshold; storage means for storing a plurality of sets of independent, spatially dependent correction factors; and means responsive to the calculated coordinates for retrieving correction factors from said storage means and for applying said correction factors to the calculated coordinates to correct said calculated coordinates wherein the correction factors of one of the sets are dislocation correction factors that correct an image for distortions due to non-linearity of the optics, photodetectors and electronics of the nuclear imaging device.

8. A nuclear imaging device according to claim 7 wherein the correction factors of one of the sets are energy window correction factors that correct for distortions due to spatial dependence of the measured total energy of interaction.

9. A nuclear imaging device according to claim 7 wherein the correction factors of one of the sets are sensitivity correction factors that correct for distortions due to nonuniformity in the response of the device with respect to incident stimuli.

10. A method for using a gamma camera having a head that includes a plurality of photodetectors for producing output signals in response to radiation stimuli which are emitted by a radiation field and which interact with the detector head and produce an event; and signal processing circuitry responsive to the output signals of the photodetectors for producing a sum signal that is a measure of the total energy of the event; said signal processing circuitry including coordinate computation circuitry responsive to said signals for producing a pair of calculated coordinate signals for each interaction which define the distorted coordinates of the event; said camera further comprising an energy correction table containing a set of spatially dependent energy windows which correspond to coordinate locations; said method comprising the steps of:

(a) producing a validation signal if said total energy of an event is within the spatially dependent energy window which corresponds to the distorted coordinates of the event; and (b) converting the distorted coordinates into relocated coordinates by applying to the distorted coordinates spatially dependent dislocation factors when a validation signal has been produced.

11. A method for using a gamma camera according to claim 10 including the step of converting the relocated coordinates into undistorted coordinates by applying to the relocated coordinates a sensitivity correction that corrects for the nonuniform stopping power of the head.

* * * * *

Disclaimer 4,588,897.—*Dan Inbar; Giora Gafni*, both of Haifa; *Ernest Grimberg*, Kiryat Bialick; *Jacob Koren*, Haifa, all of Israel. GAMMA CAMERA CORRECTION SYSTEM AND METHOD FOR USING THE SAME. Patent dated May 13, 1986. Disclaimer filed Jan. 24, 1991, by the assignee, Elscint Ltd.

The term of this patent subsequent to Jan. 4, 2001, has been disclaimed.
[ *Official Gazette May 14, 1991* ]

REEXAMINATION CERTIFICATE (1968th)
United States Patent [19]
Inbar et al.

[11] B1 4,588,897
[45] Certificate Issued  Apr. 6, 1993

[54] GAMMA CAMERA CORRECTION SYSTEM AND METHOD FOR USING THE SAME

[75] Inventors: Dan Inbar; Giora Gafni, both of Haifa; Ernest Grimberg, Kiryat Bialick; Jacob Koren, Haifa, all of Israel

[73] Assignee: Elscint, Ltd., Haifa, Israel

Reexamination Request:
No. 90/002,734, May 26, 1992

Reexamination Certificate for:
Patent No.: 4,588,897
Issued: May 13, 1986
Appl. No.: 483,741
Filed: Apr. 11, 1983

Related U.S. Application Data

[63] Continuation of Ser. No. 161,050, Jun. 19, 1980, Pat. No. 4,424,446.

[51] Int. Cl.$^5$ .............................................. G01T 1/208
[52] U.S. Cl. .............................. 250/363.07; 250/369
[58] Field of Search .................................... 250/363.07

[56] References Cited

U.S. PATENT DOCUMENTS

| | | | |
|---|---|---|---|
| 3,745,345 | 7/1973 | Muehllehner | 250/363.01 |
| 4,095,108 | 6/1978 | Inbar et al. | 250/369 |
| 4,151,416 | 4/1979 | Richey et al. | 250/363.07 |
| 4,212,061 | 7/1980 | Knoll et al. | 364/413.24 |
| 4,223,221 | 9/1980 | Gambini et al. | 250/363.07 |
| 4,298,944 | 11/1981 | Stoub et al. | 382/6 |
| 4,316,257 | 2/1982 | Del Medico et al. | 364/527 |
| 4,424,446 | 1/1984 | Inbar et al. | 250/363.07 |
| 4,588,897 | 5/1986 | Inbar et al. | 250/363.07 |

OTHER PUBLICATIONS

Alan D. Waxman et al. "Improvement of Anger Camera Images by Digital Techniques", Abstract of Paper, Journal of Nuclear Medicine, Jun. 1970, vol. II, No. 6, p. 375.

P. D. Esser, "Improvements in SPECT Technology for Cerebral Imaging"; Seminars in Nuclear Medicine; vol. XV, No. 4 (Oct. 1985), pp. 335, 336, 338-345.

B. R. Condon, "The Effect of Gamma Camera Non-Linearity of the Performance of a Limited Angle (7 Pinhole) Tomographic Imaging System"; Nuclear Instruments and Methods in Physics Research, 221 (1984) 187-191.

J. L. Moretti et al. "Mesures des performances des caméras à scintillation": Contrôle de Qualité; J. Biophys. et Méd. Nucl., 1983, 7, 1, 43-57.

P. Sharp et al. "The Usefulness of Indices Measuring Gamma Camera Non-Uniformity"; Phys. Med. Biol., 1981, vol. 26, No. 1, 149-153.

B. H. Hasegawa et al. "The Measure of a Camera-Pathways for Future Understanding"; Journal of Nuclear Medicine, vol. 22, No. 1, 78-81 (1981).

J. A. Sorenson, "Improvements in Anger Camera Performance"; Journal of Nuclear Medicine, vol. 21, No. 8, 801-802 (1980).

G. Muehllehner et al.; "Correction for Field Nonuniformity in Scintillation Cameras Through Removal of Spatial Distortion"; Journal of Nuclear Medicine, vol. 21, No. 8, 771-776 (1980).

B. E. Oppenheim, "Computer-Assisted Emission Imaging"; Journal of Nuclear Medicine; vol. 21, No. 3, 286-288 (1980).

M. L. Nusynowitz et al. "A Mathematical Index of Uniformity (IOU) for Sensitivity and Resolution"; Radiology 131:235-241, Apr. 1979.

R. Wicks et al. "Effect of Spatial Distortion of Anger Camera Field-Uniformity Correction: Concise Communication": Journal of Nuclear Medicine, vol. 20, No. 3, 252-254 (1979).

G. F. Knoll et al. "Computer Correction of Camera Nonidealities in Gamme Ray Imaging"; IEEE Transactions on Nuclear Science, vol. NS-29, No. 4, Aug. 1982, pp. 1272-1279.

N. J. Cox et al. "A Numerical Index of Gamma-Camera Uniformity"; British Journal of Radiology, 49,734, 1976.

"Information Processing In Medical Imaging," IN-SERM, 1980, Meeting Held Jul. 2-6, 1979, Paris, pp. 7, 8, 187-200.

W. L. Rogers et al., "Field-Flood Requirements For

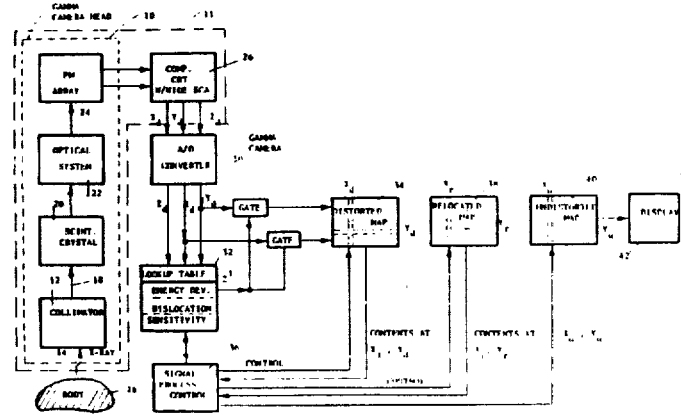

Emission Computed Tomography With An Anger Camera," *Journal of Nuclear Medicine*, vol. 23, No. 2, 1982, pp. 162-168.

Knoll, "Single-Photon Emission Computed Tomography" Proceedings of the IEEE, vol. 71, No. 3, Mar. 1983, pp. 320-329.

Marcus et al., eds., "Cardiac Imaging, A Companion to Braunwald's Heart Disease," by Ernest V. Garcia, W. B. Saunders Company, 1991, Part VIII, Ch. 55.

A. Taylor et al. eds., "Clinical Practice of Nuclear Medicine," Churchill Livingstone Inc. 1991, pp. 1-36.

B. D. Ahuluwalia, ed., "Tomographic Methods in Nuclear Medicine: Physical Principles, Instruments, and Clinical Applications" CRC Press, 1989, pp. 44-52.

S. L. Heller et al. "SPECT Instrumentation: Performance, Lesion Detection, and Recent Innovations," *Seminars In Nuclear Medicine*, vol. XVII, No. 3 (Jul.), 1987, pp. 184-189.

English et al. "SPECT: Single Photon Emission Computed Tomography: A Primer," 2d Edition, pp. 25-46.

A. E. Todd-Pokropek et al. "The Non-Uniformity of Imaging Devices and Its Impact on Quantitative Studies", Medical Radionuclide Imaging, vol. 1, proceedings of a symposium, 25-29 Oct., 1976, pp. 67-84.

"Analysis and Correction of Spatial Distortions Produced by the Gamma Camera", Spector et al., *Journal of Nuclear Medicine*, vol. 13, No. 5 (1972), pp. 307-312.

Letters to the Editor, "Analysis and Correction Distortions Produced by the Gamma Camera", by Robert A. Perry, with Author's Reply by Valerie A. Brookeman, *Journal of Nuclear Medicine*, pp. 125-126, vol. 14, No. 2.

"Online Digital Methods for Correction of Spatial and Energy Dependent Distortion of Anger Camera Images", Shabason et al., Information Processing in Medical Imaging, The University of Colorado Medical Center and the Denver VA Hospital, Jun. 27-Jul. 1, 1977, pp. 377-388.

Spector et al., Analysis and Correction of Spatial Distortions Produced by the Gamma Camera, Journal of Nuclear Medicine, Vol. 13, No. 5, pp. 307-312 (1972).

Letter to the Editor by Robert R. Perry, Journal of Nuclear Medicine, Vol. 14, No. 2, pp. 125-126 (1973).

*Primary Examiner*—Constantine Hannaher

[57] ABSTRACT

A map of a radiation field produced by a gamma camera is corrected for three types of spatially dependent errors in a manner that corrects for each error independently of the others. The errors corrected for are dislocations which result from the non-linearity of the optics, photomultipliers and electronics of the camera, energy window variations resulting from inhomogeneity of the optical system which includes the crystal, light guide, and photomultipliers, and the non-uniform sensitivity of the head resulting from the non-uniform stopping power of the crystal and collimator of the camera head. The map is corrected by obtaining a set of correction factors associated with each type of error using a calibration technique that insures independence between the various correction factors, and applying the correction factors to the map obtained in a nuclear imaging process in a way that independently corrects the map for each type of error.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to th epatent.

AS A RESULT OF REEXAMINATION, IT HAS BEEN DETERMINED THAT:

The patentability of claims 2, 5, 6, 9 and 11 is confirmed.

Claims 1, 3, 4, 7 and 10 are cancelled.

Claim 8 is determined to be patentable as amended.

New claims 12-21 and 22 are added and determined to be patentable.

8. A nuclear imaging device according to claim [7] *9* wherein the correction factors of one of the sets are energy window correction factors that correct for distortions due to spatial dependence of the measured total energy of interaction.

*12. A device according to claim 4 further comprising means for storing spatially dependent sensitivity correction factors, and further comprising means responsive to the relocated coordinates of an interaction for retrieving said sensitivity correction factors and for applying them to the interaction after the application of said energy window and dislocation correction factors.*

*13. A device according to claim 12 wherein said means responsive to an occurrence validates the interaction only if the total energy of the interaction satisfies a position dependent energy window criterion when said energy window correction factor is applied to the interaction.*

*14. A device according to claim 13 wherein said means for storing spatially dependent energy window correction factors includes means for storing energy windows whose values are dependent upon the calculated coordinates of the interaction with the device, and said position dependent energy window criterion is satisfied when the total energy of the interaction lies within the energy window at the calculated coordinates.*

*15. A device according to claim 13 wherein said means for storing spatially dependent energy window correction factors includes means for storing location dependent energy window correction factors and means for applying location dependent energy window correction factors to the total energy of the interaction to produce a corrected energy signal, and said means responsive to an occurrence includes a single channel analyzer having a fixed window and means for applying the corrected energy signal to said fixed window, and said position dependent energy window criterion is satisfied when the corrected energy signal lies within said fixed window.*

*16. A device according to claim 15 wherein said means for applying the location dependent energy window correction factor is adapted to multiply the measured total energy by the energy window correction factor to produce said corrected energy signal.*

*17. A device according to claim 15 wherein said means for applying the location dependent energy window correction factor is adapted to add the energy window correction factor to the measured total energy to produce said corrected energy signal.*

*18. A device according to claim 12 wherein the sensitivity correction factors correct for distortions due to nonuniformity in the response of the device with respect to incident stimuli.*

*19. A device according to claim 18 and also comprising a scintillation crystal wherein the sensitivity correction factors correct for non-uniform response of the crystal.*

*20. A device according to claim 18 and also comprising a gamma camera collimator wherein the sensitivity correction factors correct for non-uniform transmission of the collimator.*

*21. A device according to claim 12 wherein said means for retrieving and applying sensitivity correction factors applies each of the retrieved sensitivity correction factors to an interaction on an event-by-event basis to obtain an undistorted map of said radiation field.*

*22. A device according to claim 21 wherein numbers are stored at a plurality of locations of said undistorted map and wherein said numbers are a function of said sensitivity correction factors.*

* * * * *